United States Patent [19]

Heckele

[11] 4,064,886

[45] Dec. 27, 1977

[54] APPARATUS FOR CLEANSING ENDOSCOPES

[75] Inventor: Helmut Heckele, Knittlingen, Germany

[73] Assignee: Riwoplan Medizin-Technische Einrichtungs-Gesellschaft mbH, Knittlingen, Germany

[21] Appl. No.: 742,579

[22] Filed: Nov. 17, 1976

[30] Foreign Application Priority Data

Nov. 20, 1975 Germany .............................. 2552011

[51] Int. Cl.$^2$ .......................... B08B 3/02; B08B 3/12
[52] U.S. Cl. ................................. 134/95; 21/82 R; 21/87; 21/102 A; 134/102; 134/103; 134/169 C; 134/171; 134/184
[58] Field of Search ........... 134/166 C, 167 C, 168 C, 134/169 C, 171, 199, 58 R, 184, 22 C, 34, 1, 95, 102, 103; 21/58, 82 R, 82 H, 90, 91, 102 A, 87; 128/4, 6

[56] References Cited

U.S. PATENT DOCUMENTS

| | | | |
|---|---|---|---|
| 2,477,238 | 7/1949 | Cavi | 134/199 X |
| 3,367,154 | 2/1968 | Wyatt et al. | 134/199 X |
| 3,575,383 | 4/1971 | Coleman | 134/184 X |
| 3,638,666 | 2/1972 | Fishman | 134/184 X |
| 3,918,987 | 11/1975 | Kopfer | 134/199 X |
| 3,944,429 | 3/1976 | Trudell | 134/199 X |
| 3,963,438 | 6/1976 | Banez | 21/87 X |

Primary Examiner—Morris O. Wolk
Assistant Examiner—Arnold Turk
Attorney, Agent, or Firm—Kinzer, Plyer, Dorn & McEachran

[57] ABSTRACT

Apparatus for cleansing endoscopes, comprises a holder device, a cylindrical cleaning container, time control means for placing said holder device under timed control, a rotatable mounting for said holder device, said holder device being arranged for directing the barrel of the endoscope to be cleaned towards the interior of said cleaning container, said cleaning container being provided, for a substantial part of its length and around its circumference, with first nozzles which are connectable to a hot water line and which are orientated radially and/or at an angle to the axis of the container, with at least one succeeding circumferential series of second nozzles which are connectable to a pressurized container for containing a disinfecting liquid, and following these, with at least one further circumferential series of third nozzles to which compressed air can be applied. The cleaning container has a controllable return line to said pressurized container and an outlet having a controlled valve. The supply to the nozzles and the operation of the return line and of said outlet of said cleaning container are controllable from a central point by means of selectable programmes.

4 Claims, 1 Drawing Figure

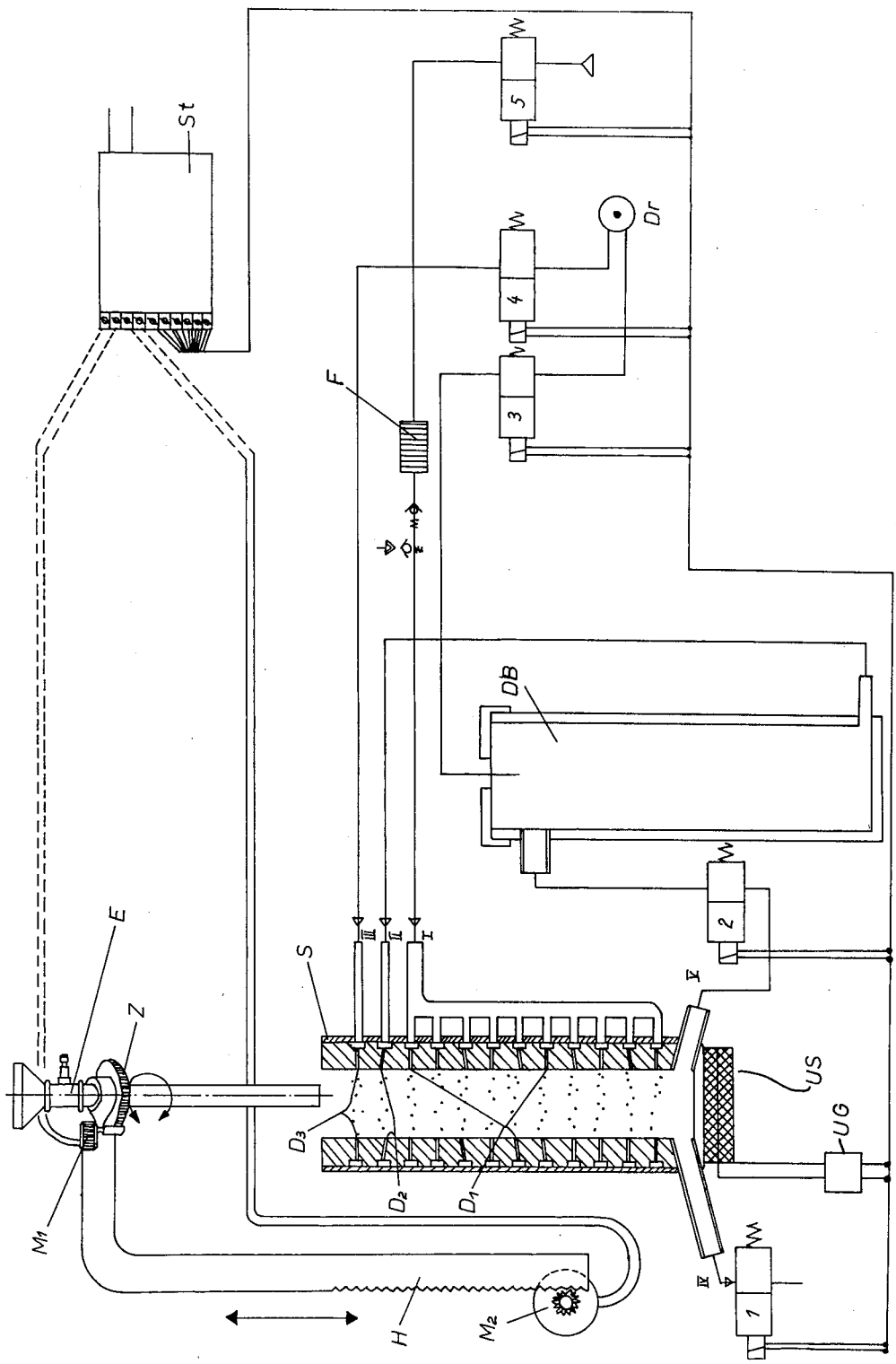

APPARATUS FOR CLEANSING ENDOSCOPES

BACKGROUND OF THE INVENTION

Due to the rapid succession of examinations called for by modern methods of clinical examination, it is necessary at the present time for endoscopes to be ready for use again as quickly as possible after each endoscope examination once they have been cleansed and disinfected. Existing manual methods of cleansing and disinfection are not satisfactory for this purpose however, particularly since the proper staff is not generally available to do the work. Nor is it possible to make use of the automatic cleansing devices which are today in widespread use for cleansing and disinfecting the general run of medical instruments since endoscopes are delicate and require particularly careful handling.

It is therefore an object of the invention to enable fast and automatic cleansing and disinfection, specifically of endoscopes, to be carried out in which the endoscopes are handled gently and without damage.

SUMMARY OF THE INVENTION

To this end, the cleansing apparatus according to the invention is characterised by a holding device which is under timed control and can be moved relative to a cylindrical cleaning container and which has a mounting, which can be driven in rotation, for an endoscope whose barrel is directed towards the interior of the cleaning container, the cleaning container being provided, over a substantial part of its height or length and around its circumference, with first nozzles which are orientated radially and/or obliquely to the axis of the container and which can be connected to a hot water line, with at least one succeeding circumferential series of second nozzles which are connectable to a pressurized container containing a disinfecting liquid, and following these with at least one further circumferential series of third nozzles to which compressed air can be applied, and in that the cleaning container has a controllable return line to the pressurised container and an outlet having a controlled valve, with the supply to the nozzles and the operation of the return line, of the outlet from the cleaning container and of the holding device being controllable from a central point by programmes which can be selected.

It is advantageous for the holding device to be so mounted that it can move vertically above the upright, cylindrical cleaning container with the endoscope suspended from it with its barrel directed downwards, or for the holding device to be arranged in a fixed position and the cleaning container to be mounted in such a way to be capable of being raised and lowered and turned. It is also possible to arrange the cleaning container with its axis horizontal and for the relative movement to take place in the axial direction of the cleaning container and the endoscope.

Using the automatic cleansing apparatus according to the invention, it is possible for an endoscope, or the optical system of an endoscope, which is to be cleansed to be suspended easily in the mount of the movable holding device and for the endoscope to be introduced into the container, and rotated on its axis and for it to remain in the cleaning container for the requisite period during which period the cleaning container can be supplied by means of the nozzles with hot water, disinfecting liquid and compressed air, following a selectable programme, thus allowing the endoscope to be automatically, quickly and thoroughly cleansed and also disinfected.

BRIEF DESCRIPTION OF THE DRAWING

In order that the invention may be more clearly understood, reference will now be made to the accompanying drawing, which shows a circuit arrangement for automatically cleansing and disinfecting an endoscope and which includes a vertical section through the cleaning container used therein.

DETAILED DESCRIPTION OF A PREFERRED EMBODIMENT

Referring now to the drawing, the cleansing apparatus shown therein consists of a cylindrical cleaning container S for cleansing and disinfecting an endoscope E. For a substantial part of its height, this cleaning container S is provided with first, vertically and circumferentially distributed nozzles D1 which are orientated radially or obliquely, i.e. at an angle other than 90°, to the axis of the container and which can be supplied from a hot water line, possibly at increased pressure, via a distribution line and annular ducts at I and via a sterile filter F and a water softener or the like. Above the nozzles D1 is provided at least one circumferential series of second nozzles D2 which can be supplied at II with a disinfecting liquid from a pressurised container DB. Finally, there is provided at least one uppermost circumferential row of third nozzles D3 which can be supplied at III with compressed air from a compressed air source DR.

Near the cleaning container S is mounted a schematically indicated holding device consisting of a bar, e.g. a rack II, which can be moved vertically parallel to container S by a motor M2 and whose upper, angled arm carries a motor M1 for a mount Z which can be driven to rotate in the horizontal plane. An endoscope E can be suspended in this mount Z above the cleaning container S, in a centralised position and with its head upwards.

At its lower end, the cleaning container S is provided with an outlet IV which can be opened or closed by a controllable valve 1. Also provided is an outlet V from which a return line provided with a controllable valve 2 leads to a pressurised container DB which holds substantially sterile or sterilising, liquid.

In certain cases, an ultrasonic vibrator US is also arranged under the bottom of the cleaning container S and this vibrator can be driven by a controllable ultrasonic generator UG.

To cleanse and disinfect an endoscope, or the optical system of an endoscope, a pneumatically, hydraulically, electromechanically or electronically operated control device ST is provided, by which the motors M1 and M2 to raise and lower the holding device II and to rotate the mount Z and the endoscope E can be switched on and off in a timed sequence. The control device ST is also provided with a number of buttons to put into operation different programmes for cleansing and disinfecting the endoscope.

The automatic cleansing apparatus can be used to put into operation individual or successive programmes, as desired, e.g. as follows:

1. After a cursory preliminary cleaning operation, if required, the endoscope E is suspended in the holder and lowered into the cleaning container S while being rotated on its axis. The valve 5 in the hot water line is opened so that the endoscope is cleaned from all directions by the nozzles D1. At the same time, valve 3 is also opened so that the endoscope E is sprayed with disinfecting liquid from nozzles D2. While this is taking place valve 1 is held open so that hot water and disinfecting liquid drain out from container S. At this time valve 2 remains closed. As the endoscope is moved into the cleaning container S, the pressure of the hot water and the disinfecting liquid and the rotation of the endoscope on its axis ensure proper cleansing and disinfection. After this, the endoscope is raised again and removed from the mount Z so that the next endoscope can be cleansed and disinfected.

2. In another programme, the valve 1 remains closed and hot water flows through nozzles D1 into the cleaning container S via valve 5, which is open, until the container is filled to the desired extent. In certain cases, the ultrasonic generator UG is switched on while this is taking place, so that the vibrations of the ultrasonic vibrator US are transmitted to the liquid in container S to assist in cleaning the endoscope which has been lowered into the cleaning container. After this, valve 1 is opened to drain the container S.

3. In the next programme the container S is closed tight and once valve 1 has been closed disinfecting liquid from pressurised container DB is fed under pressure in container DB is generated by the pressure source Dr or a pump or piston via valve 3.

4. After the endoscope has been left in the container S for a fixed period, the disinfecting liquid flows back into pressurised container DB via valve 2, which is opened.

5. When the following programme is changed to, valve 5 and valve 1 are opened again, after valve 2 has been closed, so that the endoscope can be washed again with hot water.

6. Finally, when the final programme is changed to, valve 4 is opened and compressed air, possibly warmed somewhat, is blown over the endoscope, which is now being raised, in order to blow-dry the endoscope or optical system.

It is of course possible to run programme 1 alone and to allow programmes 2 to 6 to run automatically.

I claim:

1. Apparatus for cleaning endoscopes comprising a container having a first set of nozzles connected to a source of water, a second set of nozzles connected to a source of disinfecting liquid, and a third set of nozzles connected to a source of compressed air, control valves respectively interposed between each source and the related nozzles, a rotatable mount positioned above the container and adapted to suspend the endoscope, a vertically movable support supporting the mount so that on downward movement the suspended endoscope is submerged in whilst on subsequent upward movement the endoscope emerges from the container, motor means respectively for moving the support and rotating the mount, and control means for selectively operating the motors and the valves.

2. Apparatus according to claim 1 wherein a filter and a water softener are connected between said water source and the first set of nozzles.

3. Apparatus according to claim 1, wherein said container includes at its underside an ultrasonic vibrator operable from an ultrasonic generator which is associated therewith and controlled by said control means as part of a cleaning program.

4. Apparatus according to claim 1 in which there is a return line from the container to the water source, the return line having a controllable valve therein, and in which there is an independent return line from the container to the source of disinfecting liquid, said independent return line also having a controllable valve therein.

* * * * *